United States Patent
Chen et al.

(10) Patent No.: US 7,899,154 B2
(45) Date of Patent: Mar. 1, 2011

(54) SMALL SPOT AND HIGH ENERGY RESOLUTION XRF SYSTEM FOR VALENCE STATE DETERMINATION

(75) Inventors: Zewu Chen, Schenectady, NY (US); Li Danhong, Guilderland, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 0 days.

(21) Appl. No.: 12/531,142

(22) PCT Filed: Mar. 14, 2008

(86) PCT No.: PCT/US2008/056944
§ 371 (c)(1),
(2), (4) Date: Sep. 14, 2009

(87) PCT Pub. No.: WO2008/112950
PCT Pub. Date: Sep. 18, 2008

(65) Prior Publication Data
US 2010/0046702 A1    Feb. 25, 2010

Related U.S. Application Data

(60) Provisional application No. 60/894,986, filed on Mar. 15, 2007, provisional application No. 60/953,603, filed on Aug. 2, 2007.

(51) Int. Cl.
*G01N 23/223* (2006.01)
(52) U.S. Cl. .................................................... 378/45
(58) Field of Classification Search ............ 378/42, 378/44–49, 70, 84
See application file for complete search history.

(56) References Cited

U.S. PATENT DOCUMENTS 2,540,821 A    2/1951    Harker (Continued)

FOREIGN PATENT DOCUMENTS

JP    08122500 A    5/1996

(Continued)

OTHER PUBLICATIONS

Birks L. et al: "X-ray fluorescence analysis of the concentration and valence state of sulfur in pollution samples" Spectrochimica Acta Part B, vol. 33, No. 7, 1978, pp. 305-310, XP002486663.

(Continued)

*Primary Examiner* — Irakli Kiknadze
(74) *Attorney, Agent, or Firm* — Jeffrey Klembczyk, Esq.; Kevin P. Radigan, Esq.; Heslin Rothenberg Farley & Mesiti P.C.

(57) ABSTRACT

An x-ray fluorescence technique for determining a valence state of a sample. An x-ray excitation path is provided for exciting a sample with x-rays; and an x-ray detection path is provided for detecting fluorescence emitted from the sample, and focusing the emitted fluorescence to a focal spot. The detection path may include a monochromating detection optic for focusing the fluorescence; and also may include a detector on which the focal spot is focused. The precise positions of the focal spot are sensed, from which valence states of the sample can be determined; and/or the detection optic can be rocked across certain angles of incidence, to change the Bragg conditions, thereby sensing different valence states within the sample.

20 Claims, 6 Drawing Sheets

U.S. PATENT DOCUMENTS

| | | | |
|---|---|---|---|
| 4,091,282 A * | 5/1978 | Anisovich et al. | 378/49 |
| 6,263,042 B1 | 7/2001 | Den Hartog et al. | |
| 2002/0057759 A1* | 5/2002 | Ferrandino et al. | 378/84 |
| 2004/0131146 A1* | 7/2004 | Chen et al. | 378/41 |

FOREIGN PATENT DOCUMENTS

| WO | WO 9713142 A | 4/1997 |
|---|---|---|
| WO | WO 03081222 A | 10/2003 |

OTHER PUBLICATIONS

International Search Report for PCT/US2008/056944, dated Jul. 2, 2008.

* cited by examiner

FIG. 1A $$n\lambda = 2d\sin\theta$$

$$d_{hkl} = \frac{a}{\sqrt{h^2 + k^2 + l^2}}$$

SMALL SPOT AND HIGH ENERGY RESOLUTION XRF SYSTEM FOR VALENCE STATE DETERMINATION

RELATED APPLICATION INFORMATION

This application is a national stage filing under section 371 of International Application No. PCT/US2008/056944, filed on Mar. 14, 2008, and which claims priority of U.S. Provisional application Nos. 60/894,986 filed on Mar. 15, 2007, and 60/953,603 filed on Aug. 2, 2007, the entire disclosure of each of these applications being hereby incorporated herein by reference.

TECHNICAL FIELD

The present invention relates in general to x-ray fluorescence. More particularly, the present invention relates to valence state detection using wavelength dispersive x-ray fluorescence.

BACKGROUND OF THE INVENTION

It is often desirable to determine the valence state of a selected target atom for material analysis. Valence state signifies with greater precision the chemical makeup of a sample. Different valence states of the same element are known to react differently in their environments, therefore, determining valence state can be useful in, e.g., medical diagnostics. Valence state differences from sample-to-sample can also be used to comparatively detect different sources of the material for, e.g., forensics. The present invention is directed to this problem of detecting different valence states.

SUMMARY OF THE INVENTION

The shortcomings of the prior art are overcome and additional advantages are provided by the present invention, which is in one aspect an x-ray fluorescence technique (method and/or system) for determining a valence state of a sample. An x-ray excitation path is provided for exciting a sample with x-rays. An x-ray detection path is also provided for detecting fluorescence emitted from the sample, and focusing the emitted fluorescence to a focal spot. The detection path may include a detection optic for focusing the fluorescence; and also includes a detector on which the focal spot is focused, and which detects the position of the focal spot, from which the valence state of the sample can be determined.

The detection path detects the position of a focal spot for a single sample, or comparatively between different samples, thereby determining the valence state absolutely for the same sample or comparatively for different samples. The detection path may implement knife-edge scanning; pin-hole scanning; slit scanning; and/or a position sensitive/area detector to detect the position of the focal spot.

The excitation path may include a focusing excitation optic for collecting x-rays from an x-ray source and focusing the x-rays onto the sample; and the detection optic may comprise a doubly curved monochromating optic for collecting a large solid angle of fluorescence from the sample and focusing a narrowed band fluorescence to a focal point on the detector.

In another aspect of the invention, an x-ray fluorescence technique (method and/or system) is provided for determining a valence state of a sample. An x-ray fluorescence system for determining valence state includes an x-ray excitation path for exciting a sample with x-rays; with an x-ray detection path for detecting fluorescence emitted from the sample; the detection path comprising a detection optic for focusing the fluorescence to a detector according to Bragg conditions; wherein rocking the detection optic between at least two angles of incidence from the sample changes the Bragg conditions to allow detection of at least one valence state within the sample.

The excitation path may include a focusing excitation optic for collecting x-rays from an x-ray source and focusing the x-rays onto the sample; and the detection optic may comprise a doubly curved monochromating optic for collecting a large solid angle of fluorescence from the sample and focusing a narrowed band fluorescence to a focal point on the detector.

Additional features and advantages are realized according to the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in connection with the accompanying drawing in which:

DESCRIPTION OF THE INVENTION

Polycapillary and doubly curved crystal (DCC) optics coupled with a small spot x-ray source provide a small spot and high energy resolution XRF system. This approach can be used to identify the valence state of a selected target atom in a sample under study using an innovative detection technique.

Figure 1A:
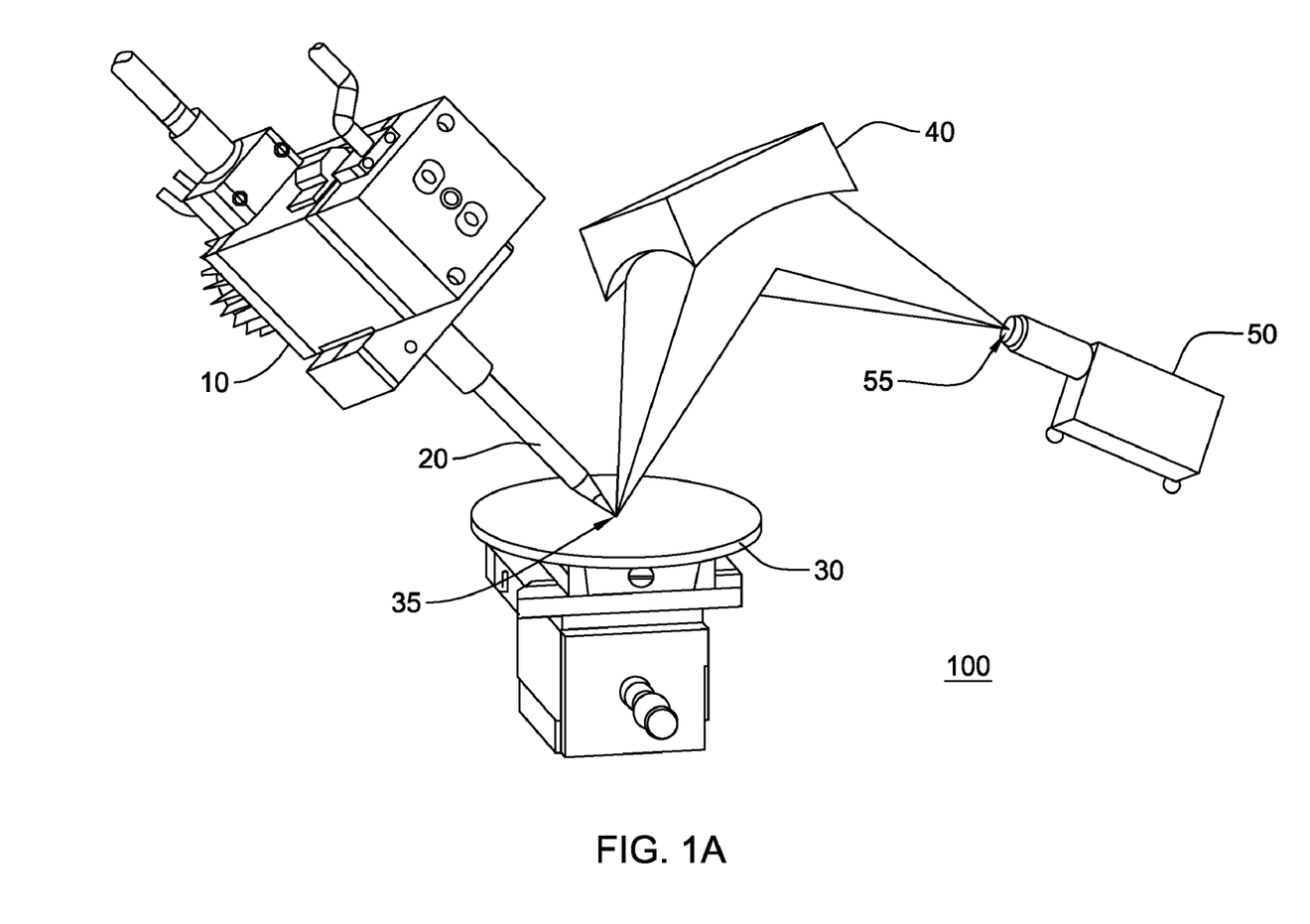
FIGS. 1a-b depict an exemplary x-ray fluorescence system, including a focusing excitation optic and a doubly curved crystal, monochromating detection optic system operating according to Bragg conditions.

In accordance with the present invention, FIG. 1 shows fluorescence system 100 having an integrated x-ray source 10 coupled with focusing optic 20 to stimulate a region 35 of sample 30. Resultant fluorescence is detected over a large angle using a collection optic 40, which collects fluorescence from the sample and focuses the fluorescence to a focal spot 55 at detector 50 (e.g., an energy sensitive detector, area detector, or a counting detector).

The x-ray beam excitation can be effected by the focusing optics (e.g., polycapillary and/or monochromating) and optic/source combinations such as those disclosed in commonly assigned, X-Ray Optical Systems, Inc. U.S. Pat. Nos. 7,110,506; 7,072,439; 7,035,374; 6,934,359; 6,285,506; 5,192,869; 5,175,755; 5,497,008; 5,745,547; 5,570,408; and 5,604,353. These patents are each incorporated by reference herein in their entirety.

Figure 1B:
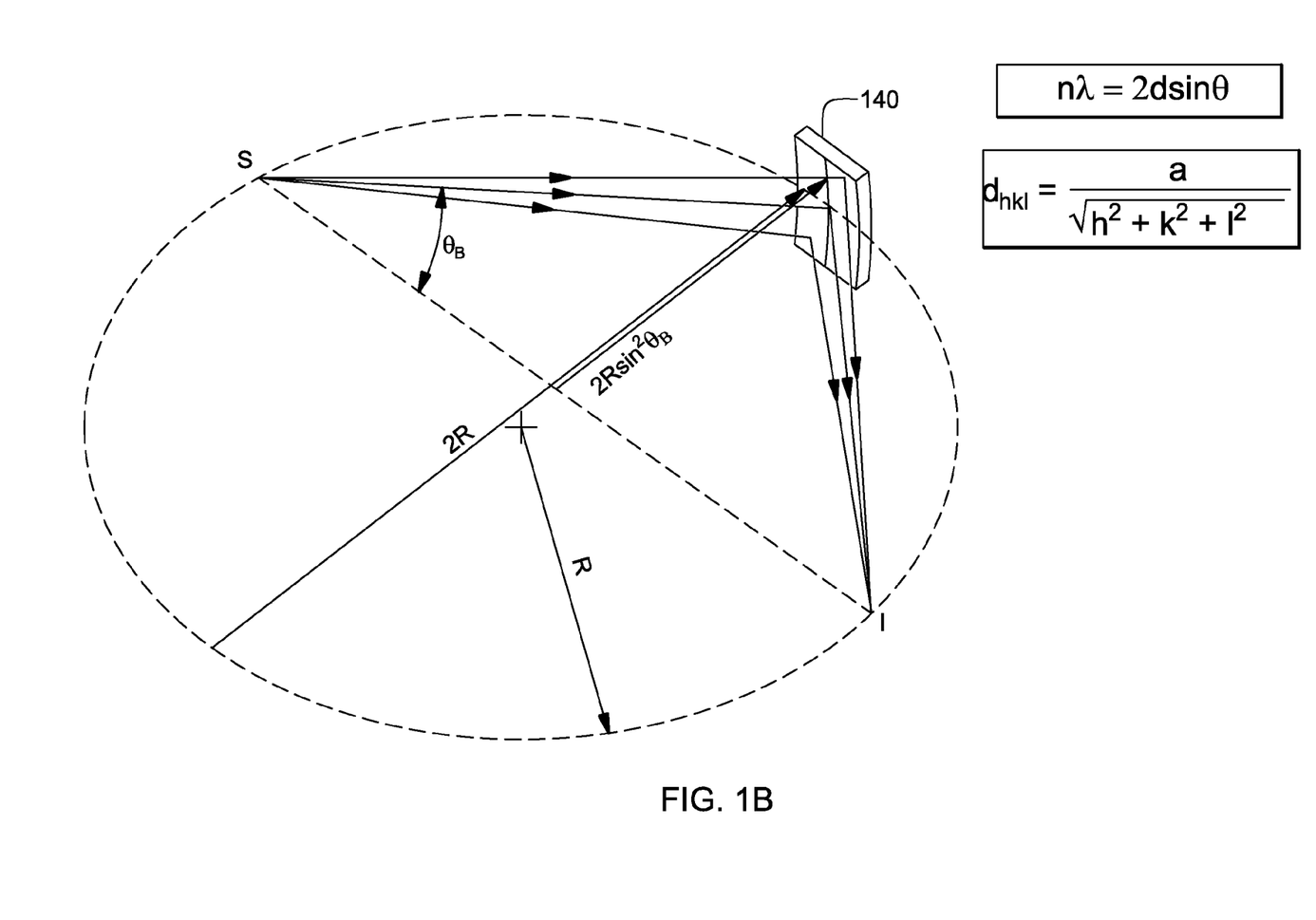

The collection optic can in one example be a singly- or doubly-curved crystal, monochromating optic, e.g., as disclosed in above-incorporated U.S. Pat. Nos. 7,035,374 and 6,285,506; and in other examples can be the focusing polycapillary optics mentioned above, focusing multi-layer monochromating optics, or equivalents or combinations thereof. The monochromating versions of these optics operate based on Bragg diffraction (as disclosed schematically in FIG. 1b with respect to optic 140) and can provide wavelength dispersive, point-to-point, line-to-line, line-to-point, or point-to-line focusing of fluorescence from a sample to a detector as shown. The monochromating function of the optic can be designed to narrow the energy bandwidth around a fluorescence line of interest (for example, Iron or Uranium fluorescence).

The ability to provide an improved, lower cost analysis capability depends to a large extent upon source/optic technology. A compact, low cost electron-bombardment x-ray source is shown (e.g., Oxford 5011) in the Figures herein. In this type of tube, an electron gun/filament is heated (by applying a voltage) to a temperature such that electrons are thermally emitted. These emitted electrons are accelerated by an electric potential difference to an anode, which is covered with target material, where they strike within a given surface area of the anode. Divergent x-rays are emitted from the anode as a result of the collision between the accelerated electrons and the atoms of the target. To control the spot size, an excitation optic 20 may be positioned between the source and the sample. This powerful combination of a low cost, low power (~50 keV, 50 W power) compact tube coupled with a focusing excitation optic provides the necessary x-ray flux to a sufficiently small spot on the sample for the techniques proposed herein.

The present inventors have discovered that valence state changes impact the fluorescence pattern focused on the detector 50 by optic 40. For different valence states, the energy of the narrowed fluorescence line is slightly different. This difference in energy slightly changes the Bragg diffraction conditions of the optic, causing a shift of focal spot 55.

Absolute valence state within the sample, or differences from sample-to-sample, can therefore be detected by slight shifts in the focal spot 55 on the detector, while all other conditions are held substantially constant; or normalized (e.g., position) to ensure that the observed focal spot position changes are not due to any system changes, but rather are due to valence state changes. These slight changes of the focal spot position can be determined using a knife-edge scanning method; pin-hole scanning method; slit scanning method; or by using a position sensitive/area detector. Any other techniques for detecting focal spot position/shift fall within the scope of the invention.

Calibration of the system for absolute and/or comparative valence state measurements can be accomplished using sample "standards" having known valence states, and determining their respective focal spot positions.

Exemplary techniques for determining the valence state are presented below for Iron (Fe) and Uranium (U).

Iron (Fe) Example

Figure 2A:
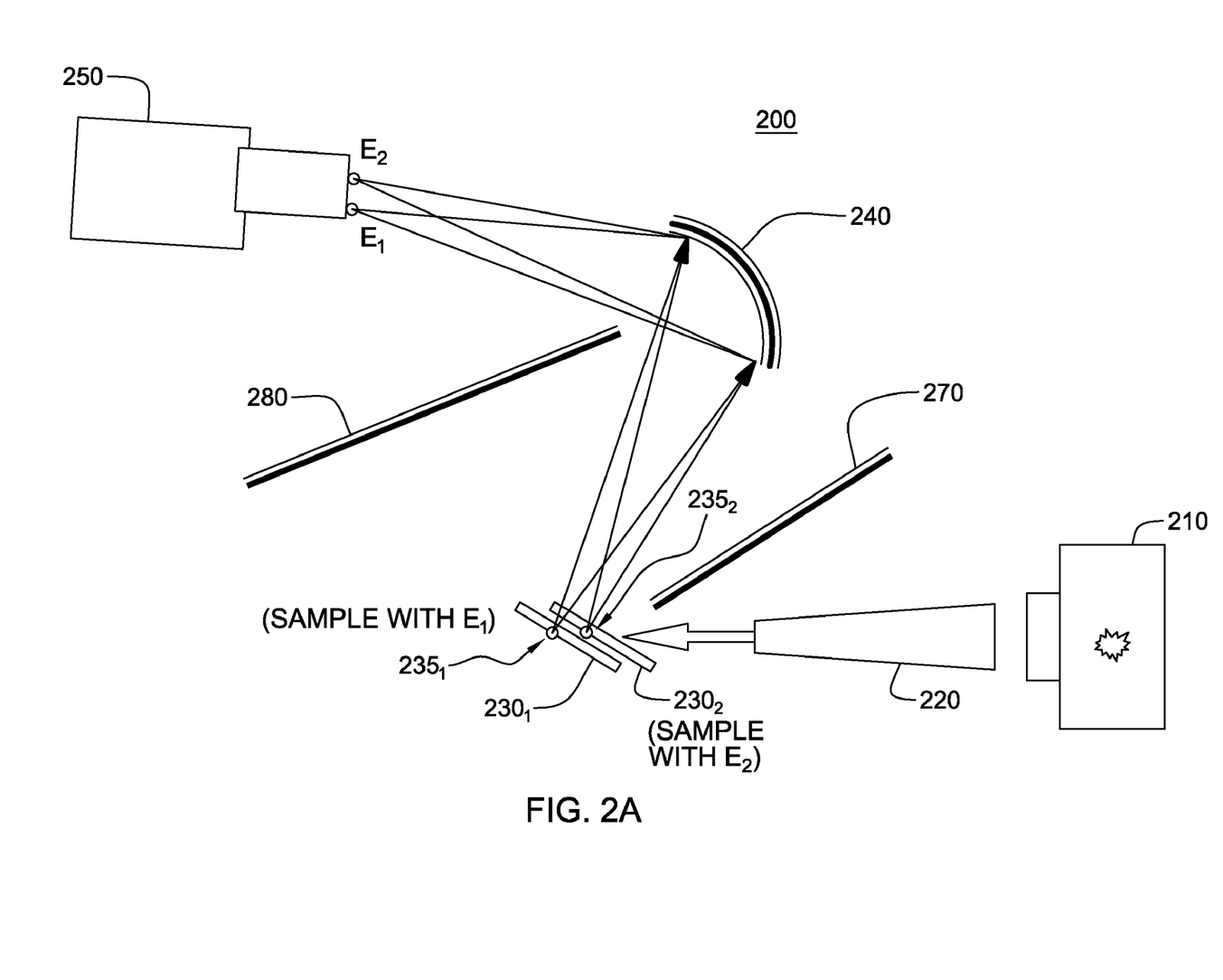
FIGS. 2a-b show a schematic and results of detecting focal spot shift sensing for valence state determination.
Figure 2B:
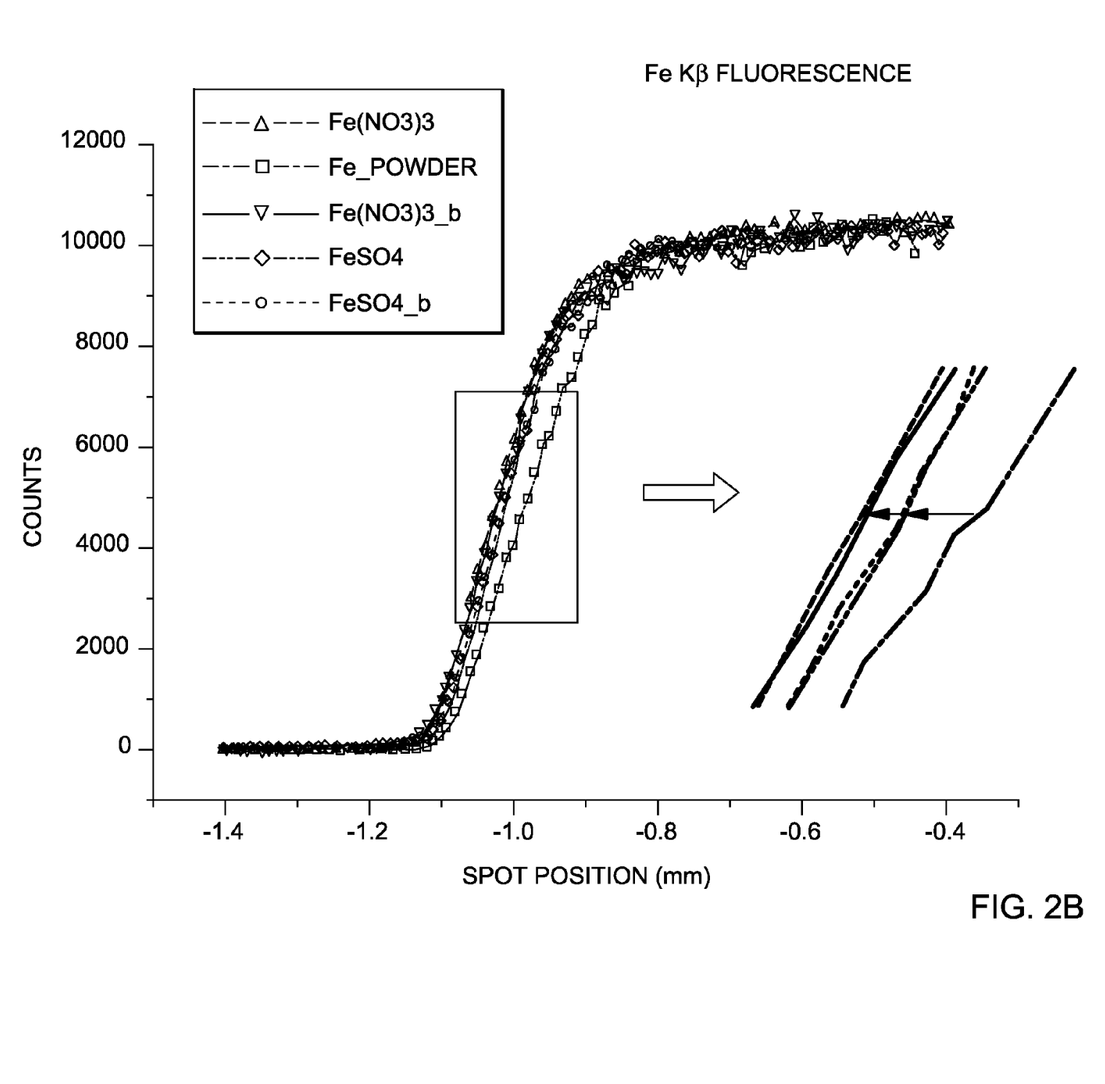

FIGS. 2a-b depict a schematic, and results of focal spot shift sensing across different analyte valence states, whereby the presence of 5 Fe analytes is detected by measured spot shift, in accordance with the techniques of the present invention, and those disclosed in the co-pending U.S. Patent Application entitled SMALL SPOT AND HIGH ENERGY RESOLUTION XRF SYSTEM FOR VALENCE STATE DETERMINATION, Ser. No. 60/894,986, Filed Mar. 15, 2007, the entirety of which is incorporated herein by reference.

In this system 200, a Cu Kα x-ray beam is chosen as the excitation beam in source 210, focused by a polycapillary optic 220. The focusing beam with a 45 µm spot size strikes the sample 230, and x-ray fluorescence is produced. A specially designed doubly curved crystal optic 240 based on Bragg diffraction can be used to collect the Kβ fluorescence of Iron (Fe) from the sample and focus the fluorescence to a focal point with less than 200 µm spot size. The Kβ fluorescence may be measured instead of conventional Kα fluorescence due to the fact that Kβ x-ray is more sensitive to the valence state.

In the example shown in FIG. 2a, two samples are shown $230_1$ and $230_2$, with respective focal points $235_1$ and $235_2$ corresponding to two different energies E1 and E2. Two different locations are shown, because alignment to the particular input focal point corresponding to energy (E1, E2) may be necessary, while optic 240 remains fixed. A sample can be "scanned" and aligned according to its proper input focal point; after which the appropriate focal spot measurement can be made at the detector 250 (i.e., indicating the correct valence state according to prior system calibration).

The focal point position of the DCC optic shifts slightly if the Bragg angle changes. For the samples with different valence states, the optic collects the fluorescence with slightly different energies corresponding to the different Bragg angles. This results in the focal point positions being slightly shifted. In this way, the valence state of the samples can be determined by measuring the spatial shift in the x-ray spot at the detector 250. A spatial shift of around 10 µm was measured between respective samples of Fe0, Fe+2, and Fe+3 (FIG. 2b).

In order to improve the energy resolution, the DCC optic can be designed for larger Bragg angle diffraction, providing a narrower energy bandwidth. The diffraction plane of the DCC can be chosen from the higher order planes like Ge (333). In addition, output focal spot size of the DCC is directly related to resolution. One particular set of DCC design parameters is as follows:

Crystal Ge(333)
Input and output focal distances: 107 mm
Bragg angle: 55 degrees
Energy peak at 7.06 keV
Spot size: 200 µm Shielding 270 and 280 can also be provided to isolate the excitation and detection paths.

Uranium (U) Example

For different valence states, the energies of the U L fluorescent lines have also been found to be different. The difference is typically on the order of 1 eV. However, this difference is too small to detect in conventional x-ray spectrometry. To detect this difference, an ultra-high energy resolution doubly curved crystal can be used to identify the U valence state (not depicted, but similar to the technique discussed above with reference to FIGS. 2a-b).

There are three strong L lines from U atoms: $L_{\alpha 1}$, $L_{\beta 1}$ and $L_{\beta 2}$. The $L_{\alpha 1}$ and $L_{\beta 1}$ lines both result from the electron transitions between M and L shells. The $L_{\beta 2}$ line is due to the transition of $N_V$ shell to $L_{III}$ shell. Therefore the energy level (16.428 keV) of the $L_{\beta 2}$ line is more sensitive to the valence state.

A 10 µm excitation beam from a focusing polycapillary optic excites the Uranium sample. The DCC will be aligned to the focal spot and the $L_{\beta 2}$ fluorescence from U atoms is focused to a spot on the detector. A slight energy change of the $L_{\beta 2}$ line due to the change of valence state within the sample, or sample-to-sample, will cause the shift of focal spot in space. A detector with a knife edge can be used to detect the location of the focal spot, which corresponds to the valence state.

A high energy-resolution toroidal DCC can be used to focus U $L_{\beta 2}$ x-rays. The focal spot size and energy resolution of the DCC properly determined and designed. The DCC is designed to have an energy resolution of better than 5 eV at 16.400 keV. With this energy resolution, a peak shift of less than 1 eV can be detected.

Changes in the focal spot position can be more easily detected by designing the optic to produce a longer focal length. With such a design, the precision requirements of the detection can be reduced.

Detection Optic Rocking

Figure 3A:
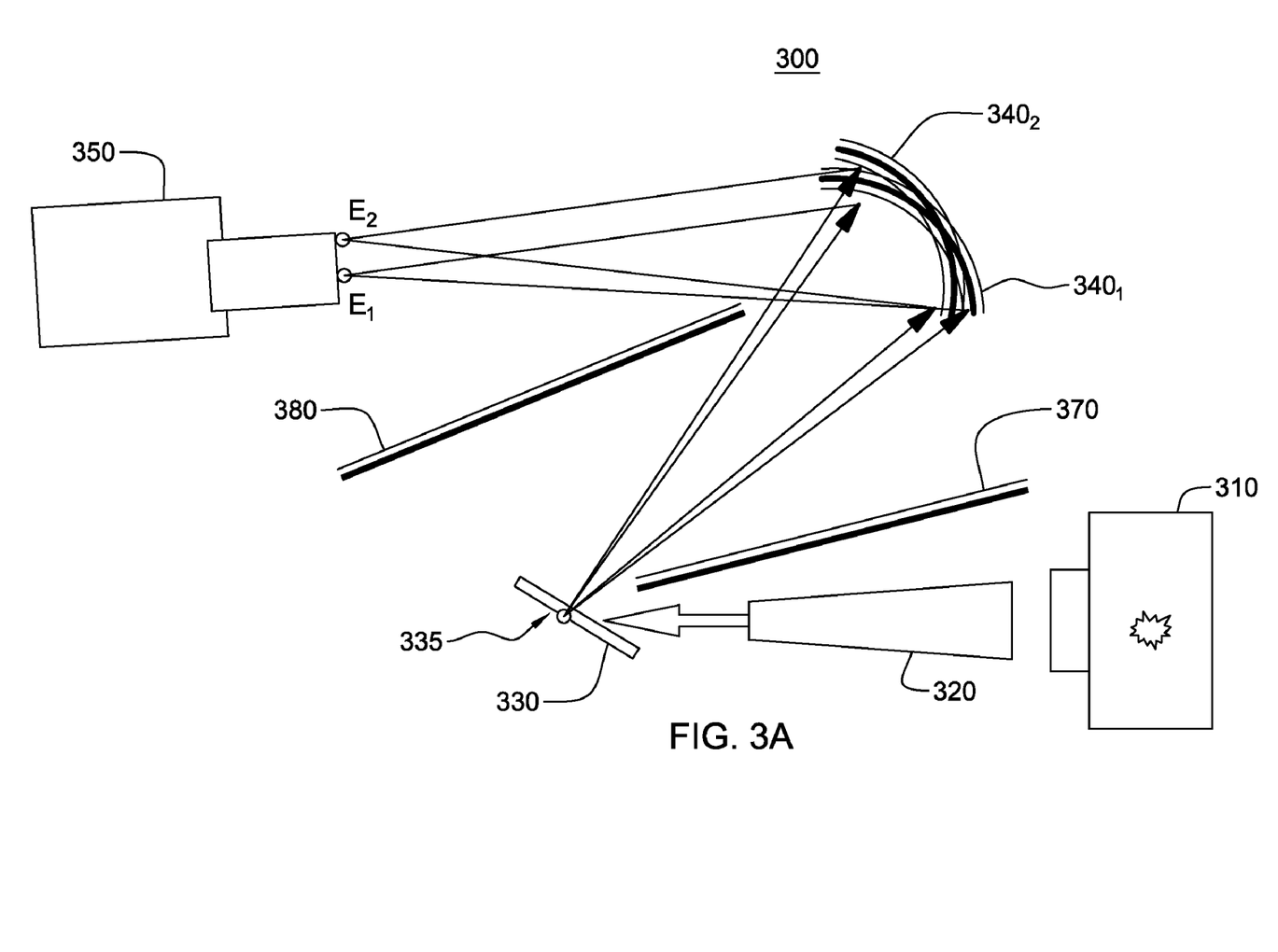
FIGS. 3a-b show a schematic and results of optic rocking across a sample for sensing different valence states.
Figure 3B:
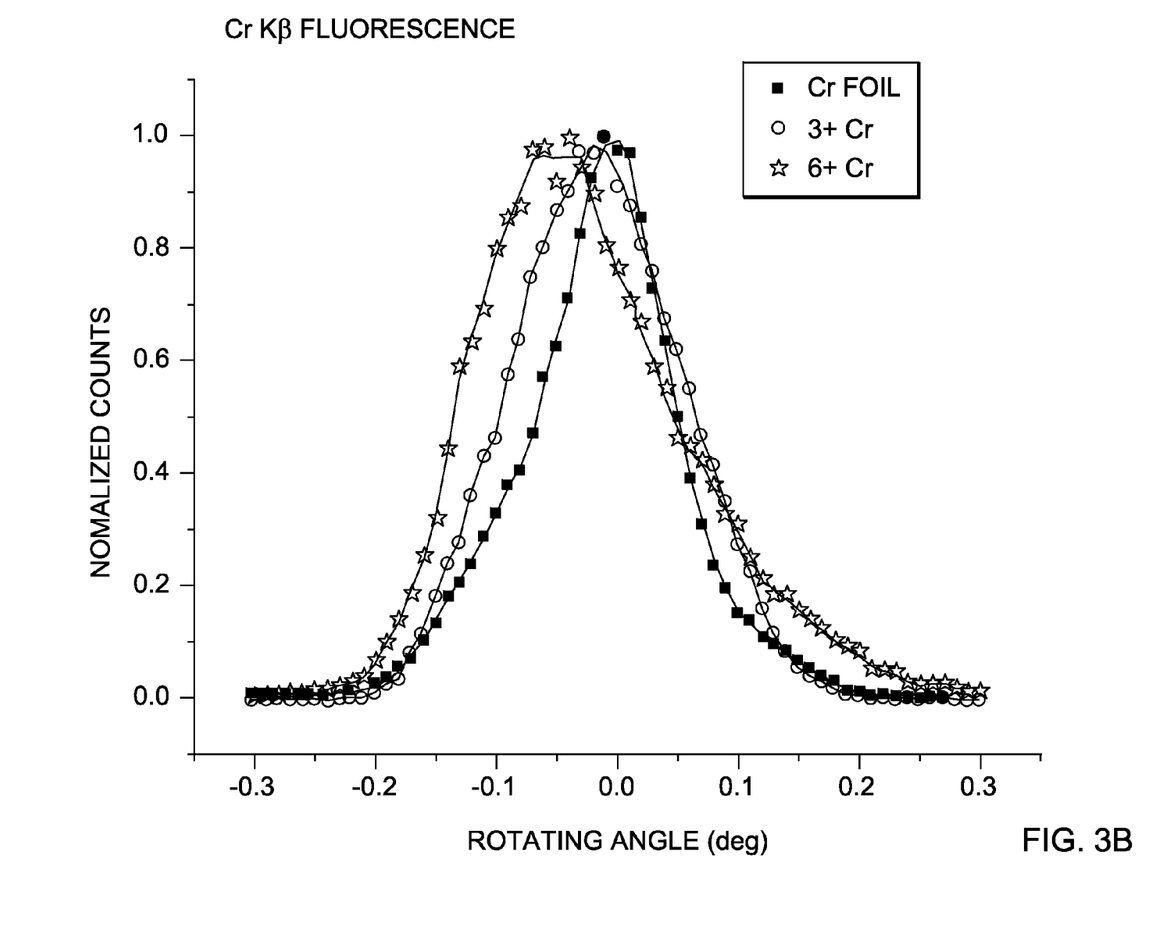

FIGS. 3a-b depict a schematic, and results of rocking the detection optic between positions $340_1$ and $340_2$ across angles of incidence, whereby the presence of 3 Cr analytes (Cr foil; Chromium Nitrate Nonahydrate; and Ammonium Dicromate $(NO_4)_2Cr_2O_7$) can be detected by the resultant changes of the Bragg conditions; in accordance with the techniques of the present invention, and those disclosed in the co-pending U.S. Patent Application entitled SMALL SPOT AND HIGH ENERGY RESOLUTION XRF SYSTEM FOR VALENCE STATE DETERMINATION BY ROCKING A FOCUSING, MONOCHROMATING COLLECTION OPTIC, Ser. No. 60/953,603 filed Aug. 2, 2007, the entirety of which is incorporated herein by reference. The term "rocking" is broadly used herein to connote any intentional rocking or other similar movement of optic 340 between different positions to affect the Bragg conditions.

In this system 300, an excitation beam from source 310 is focused by a polycapillary optic 320. The focusing beam strikes the sample 330 at sample spot 335, and a resultant focal point appears at the detector 350.

According to prior system calibration (analogous to FIG. 2a above), the resultant focal spot shifts at the detector indicate different energies (E1 and E2), and therefore different valence states are present within the sample. One particular set of DCC design parameters is as follows:

Crystal Ge(333)
Input and output focal distances: 200 mm
Bragg angle: 73 degrees
Energy peak at 5.94 keV
Spot size: 300 μm Shielding 370 and 380 can also be provided to isolate the excitation and detection paths.

In summary, polycapillary and doubly curved crystal (DCC) optics coupled with a small spot x-ray source provide a small spot and high energy resolution XRF system. This experimental approach can be used to identify the valence state of a selected target atom using an innovative detection technique. The Cu Kα x-ray beam can be chosen as the excitation beam, focused by a polycapillary optic. A specially designed DCC optic can be used to determine the valence state of an element. The samples of Fe0, Fe+2, Fe+3, Cr0, Cr+3, and Cr+6 were measured for valence state determination.

In accordance with the invention, as implied from above, the techniques of focal spot sensing of FIGS. 1 and 2 can be combined with the rocking techniques of FIG. 3.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray fluorescence system for determining a valence state of a sample, comprising:

an x-ray excitation path for exciting a sample with x-rays;
   an x-ray detection path for detecting fluorescence emitted from the sample, and focusing the emitted fluorescence to a focal spot;
      the detection path comprising a detection optic for focusing the fluorescence; and
      the detection path further comprising a detector on which the focal spot is focused, and which detects the position of the focal spot, from which the valence state of the sample is determined.

2. The x-ray fluorescence system of claim 1, wherein the detection path detects the position of a focal spot for a single sample, or comparatively between different samples, thereby determining the valence state absolutely for the same sample or comparatively for different samples.

3. The x-ray fluorescence system of claim 1, wherein the detection path implements knife-edge scanning; pin-hole scanning; slit scanning; and/or a position sensitive/area detector to detect the position of the focal spot.

4. The x-ray fluorescence system of claim 1, wherein the excitation path includes a focusing excitation optic for collecting x-rays from an x-ray source and focusing x-rays onto the sample.

5. The x-ray fluorescence system of claim 1, wherein the detection optic comprises a doubly curved monochromating optic for collecting a large solid angle of fluorescence from the sample and focusing the fluorescence to a focal point on the detector.

6. The x-ray fluorescence system of claim 5, wherein the doubly curved monochromating optic is a doubly curved crystal optic or doubly curved multi-layer optic.

7. An x-ray fluorescence method for determining a valence state of a sample, comprising:

exciting a sample with x-rays;
   detecting fluorescence emitted from the sample, and focusing the emitted fluorescence to a focal spot;
   the detecting comprising using a detection optic for focusing the fluorescence; and
   the detecting further comprising using a detector on which the focal spot is focused, and which detects the position of the focal spot, from which the valence state of the sample is determined.

8. The x-ray fluorescence method of claim 7, comprising detecting the position of a focal spot for a single sample, or comparatively between different samples, thereby determining the valence state absolutely for the same sample or comparatively for different samples.

9. The x-ray fluorescence method of claim 7, wherein the detecting includes knife-edge scanning; pin-hole scanning; slit scanning; and/or position sensitive/area detecting to detect the position of the focal spot.

10. The x-ray fluorescence method of claim 7, wherein the exciting includes using a focusing excitation optic for collecting x-rays from an x-ray source and focusing x-rays onto the sample.

11. The x-ray fluorescence method of claim 7, wherein the detecting includes using a doubly curved monochromating optic for collecting a large solid angle of fluorescence from the sample and focusing the fluorescence to a focal point on the detector.

12. The x-ray fluorescence method of claim 11, wherein the doubly curved monochromating optic is a doubly curved crystal optic or doubly curved multi-layer optic.

13. An x-ray fluorescence system for determining a valence state of a sample, comprising:
   an x-ray excitation path for exciting a sample with x-rays;
   an x-ray detection path for detecting fluorescence emitted from the sample;
      the detection path comprising a detection optic for focusing the fluorescence to a detector according to Bragg conditions; and
      wherein rocking the detection optic between at least two angles of incidence from the sample, changes the Bragg conditions to allow detection of at least one valence state within the sample.

14. The x-ray fluorescence system of claim 13, wherein the excitation path includes a focusing excitation optic for collecting x-rays from an x-ray source and focusing x-rays onto the sample.

15. The x-ray fluorescence system of claim 13, wherein the detection optic comprises a doubly curved monochromating optic for collecting a large solid angle of fluorescence from the sample and focusing the fluorescence to a focal point on the detector.

16. The x-ray fluorescence system of claim 15, wherein the doubly curved monochromating optic is a doubly curved crystal optic or doubly curved multi-layer optic.

17. An x-ray fluorescence method for determining a valence state of a sample, comprising:
   exciting a sample with x-rays;
   detecting fluorescence emitted from the sample
      including focusing the fluorescence to a detector according to Bragg conditions with a detection optic; and
      rocking the detection optic between at least two angles of incidence from the sample, thereby changing the Bragg conditions to allow detection of at least one valence state within the sample.

18. The x-ray fluorescence method of claim 17, wherein the exciting includes using a focusing excitation optic for collecting x-rays from an x-ray source and focusing x-rays onto the sample.

19. The x-ray fluorescence method of claim 17, wherein the detection optic comprises a doubly curved monochromating optic for collecting a large solid angle of fluorescence from the sample and focusing the fluorescence to a focal point on the detector.

20. The x-ray fluorescence method of claim 19, wherein the doubly curved monochromating optic is a doubly curved crystal optic or doubly curved multi-layer optic.

* * * * *